US00PP35451P2

(12) United States Plant Patent
Clark

(10) Patent No.: US PP35,451 P2
(45) Date of Patent: Oct. 31, 2023

(54) ***COLEUS* PLANT NAMED 'UF20-103-3'**

(50) Latin Name: *Coleus scutellarioides*
Varietal Denomination: UF20-103-3

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 17/803,900

(22) Filed: Jan. 13, 2023

(51) Int. Cl.
*A01H 5/02* (2018.01)
*A01H 6/50* (2018.01)

(52) U.S. Cl.
USPC ..... Plt./469

(58) Field of Classification Search
USPC ..... Plt./263.1, 469
See application file for complete search history.

(56) References Cited

U.S. PATENT DOCUMENTS

PP34,041 P2 3/2022 Clark

*Primary Examiner* — Karen M Redden
(74) *Attorney, Agent, or Firm* — Koenig IP Works, PLLC; Katherine Koenig

(57) ABSTRACT

A new and distinct cultivar of *Coleus* (*Coleus scutellarioides*) plant named 'UF20-103-3', selected for having a combination of desirable traits that make it well-suited for use as an annual plant in the summer landscape. 'UF20-103-3' was selected for its consistent foliage color patterning, and also for its fast growth rate and vigor in the greenhouse and landscape. 'UF20-103-3' has ruffled, highly lobed foliage that is predominantly dark red with consistent yellow green accents and leaf margins. 'UF20-103-3' maintains these contrasting colors and patterns in both sun and shade. 'UF20-103-3' is upright and spreading in habit, but it is highly branched, growing wider than it does tall.

5 Drawing Sheets

Genus and species: *Coleus scutellarioides*.
Cultivar denomination: 'UF20-103-3'.

CROSS-REFERENCE TO RELATED APPLICATIONS

N/A.

ACKNOWLEDGEMENT OF FEDERAL RESEARCH SUPPORT

N/A.

BACKGROUND OF THE NEW CULTIVAR

The invention relates to a new and distinct cultivar of *Coleus* plant named 'UF20-103-3'. The new cultivar 'UF20-103-3' originated from an open pollination conducted in May-November 2019 in Citra, Florida, between the female *Coleus* plant 'UF17-73-7' (unpatented) and an unknown male *Coleus* plant. A single seedling was chosen in May 2020 for further asexual propagation in Gainesville, Florida.

The new cultivar 'UF20-103-3' has been reproduced asexually for over 18 months through vegetative meristem tip cuttings and has been found to retain its distinctive characteristics through successive asexual propagations. 'UF20-103-3' was first propagated asexually by vegetative meristem tip cuttings in May 2020 in Gainesville, Florida, and has remained true-to-type since that time.

Plant Breeder's Rights for the new cultivar 'UF20-103-3' have not been applied for, and 'UF20-103-3' has not been made publicly available more than one year prior to the filing date of this application.

When compared to the female parent 'UF17-73-7', 'UF20-103-3' has large highly lobed ruffled leaves that are slightly longer than they are wide and are predominantly dark red with yellow green margins. In contrast, 'UF17-73-7' has smaller leaves that are twice as long than they are wide and are colored dark maroon with dark green margins and predominant pink mid-veins. 'UF20-103-3' has a vigorous upright and spreading habit that is well-branched, whereas 'UF17-73-7' is less vigorous and more upright in habit with less lateral branching and a less spreading habit.

The new cultivar 'UF20-103-3' was selected for its consistent foliage color patterning, and also for its fast growth rate and vigor in the greenhouse and landscape. 'UF20-103-3' has foliage that is predominantly dark red with consistent yellow green leaf margins. Normally this color combination changes in either full sun (predominantly to dark brick red) or full shade (predominantly to brownish red), with the consistent loss of the distinctive yellow green leaf margins. 'UF20-103-3' is exceptional because it maintains consistent dark red foliage color and bright yellow green margins in both sun and shade. Vegetative cuttings from 'UF20-103-3' form roots in one week and consistently produce vivid pink color in the greenhouse.

SUMMARY OF THE INVENTION

The new cultivar 'UF20-103-3' has not been observed under all possible environmental conditions. The phenotype of the new cultivar may vary with variations in environment and cultural practices such as temperature, light intensity, fertilization, irrigation, and application of plant growth regulators without any change in genotype.

The following are the most outstanding and distinguishing characteristics of 'UF20-103-3' when grown under normal horticultural practices in Gainesville, Florida: 'UF20-103-3' has the combination of vigorous, upright and spreading growth habit, excellent heat tolerance, and consistent multi-colored leaves that are significantly different than other *Coleus* plants; it has superior stability in foliage color in both sun and shade conditions, and it has a vigorous growth rate with excellent lateral branching, making it suitable for propagators and producers; and 'UF20-103-3' has been observed to have long-season performance in landscape trials in Gainesville, Florida.

DESCRIPTION OF THE FIGURES

This new *Coleus* plant is illustrated by the accompanying photographs, which show the plant's form and foliage. The colors shown are as true as can be reasonably obtained by conventional photographic procedures.

FIG. 2 shows the growth habit, form, and foliage of the new *Coleus* cultivar;

FIG. 3 shows a close-up view of the foliage of the new *Coleus* cultivar;

FIG. 4 shows the adaxial side of an immature leaf (left) and a mature leaf (right) of the new *Coleus* cultivar, with corresponding R.H.S. color designations; and FIG. 5 shows the abaxial side of an immature leaf (left) and a mature leaf (right) of the new *Coleus* cultivar, with corresponding R.H.S. color designations.

DETAILED BOTANICAL DESCRIPTION OF THE CULTIVAR

Figure 1:
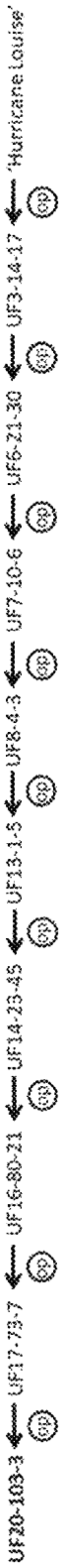
FIG. 1 shows the pedigree of the new *Coleus* cultivar 'UF20-103-3' as shown and described herein.
Figure 2:
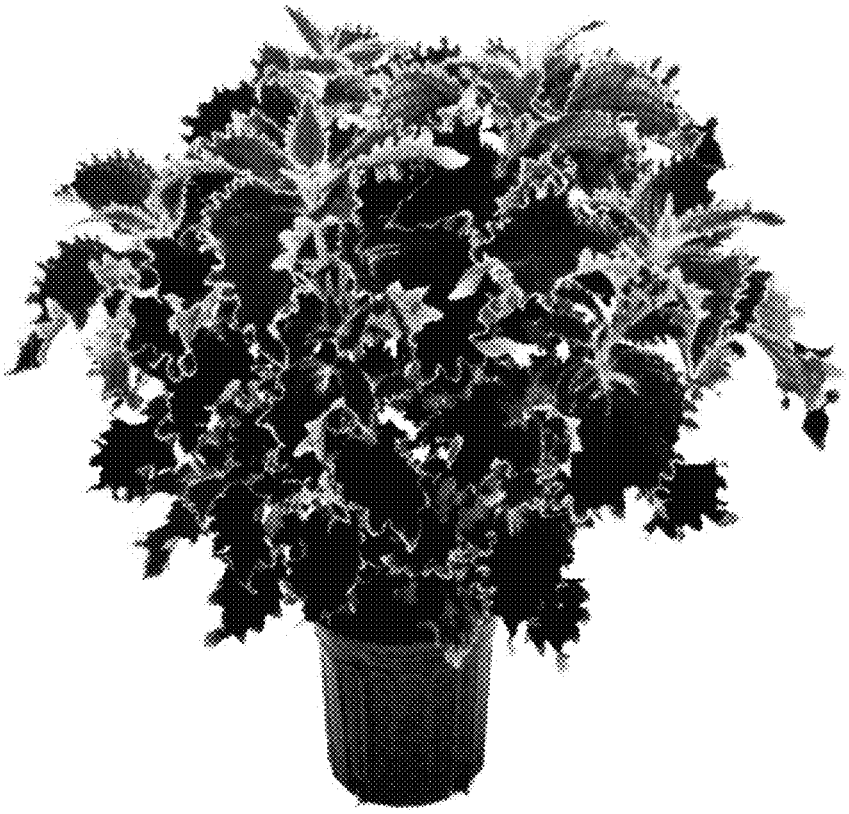
FIGS. 2-5 were taken from plants grown eight weeks from unrooted cuttings in July-September 2022 in a glass-covered greenhouse in Gainesville, Florida.
Figure 3:
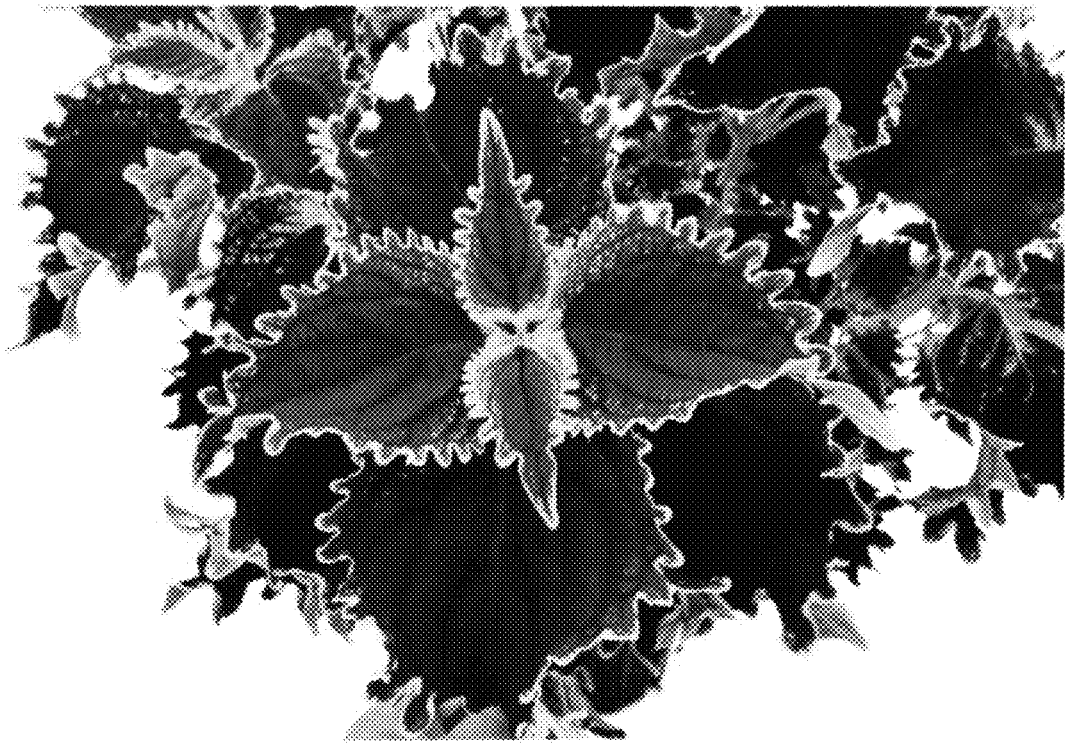
Figure 4:
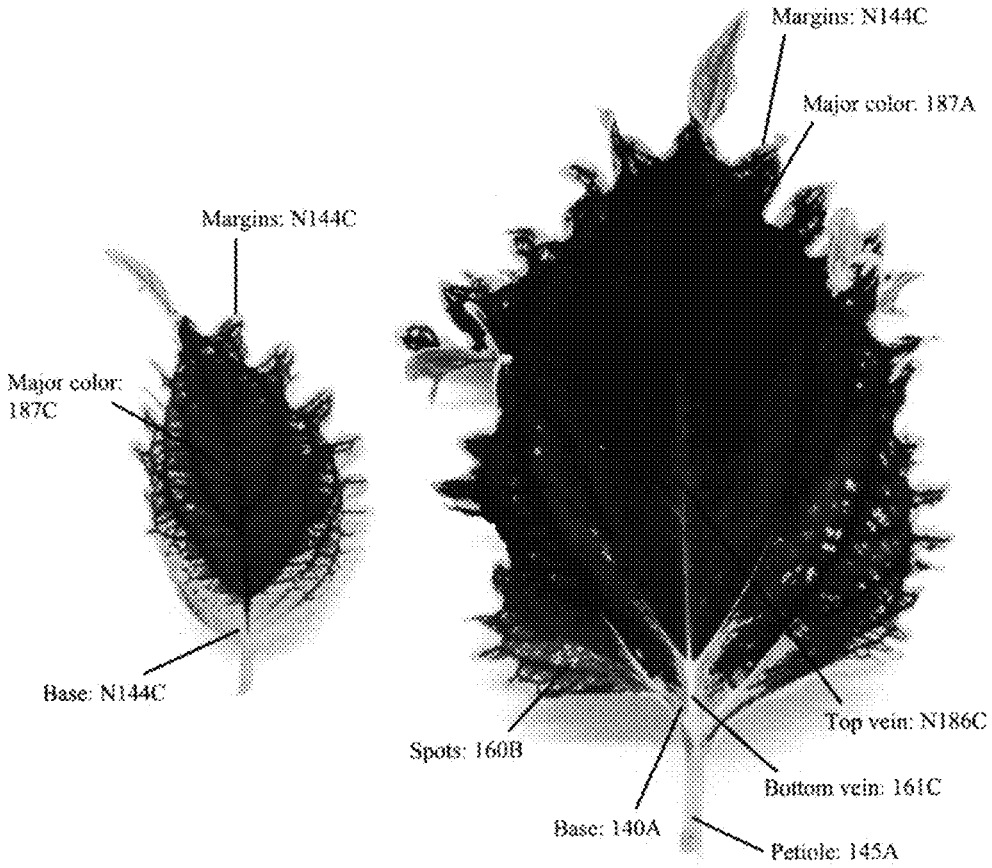
Figure 5:
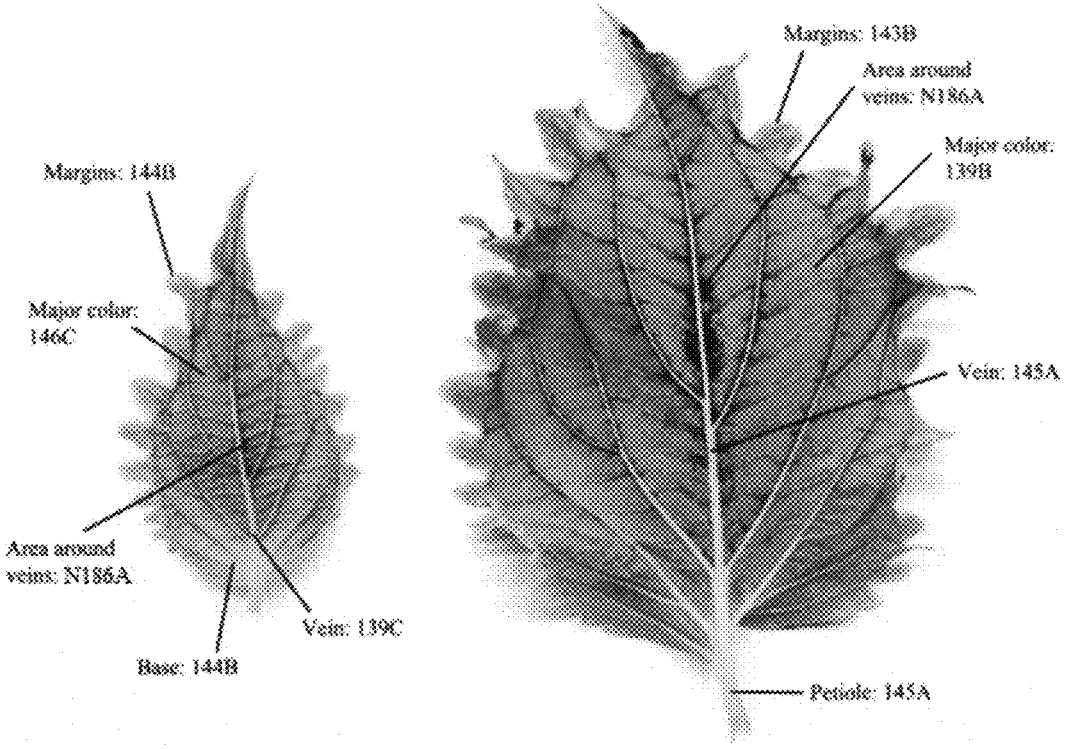

Foliage color was determined under full sun conditions in the middle of the day in a glass-covered greenhouse. Color references are to The R.H.S. Colour Chart of The Royal Horticultural Society of London (R.H.S.), 2007 5th Edition. *Coleus* leaves are rarely one solid color but encompass hues, shades and tints, and color patterns differ from one genotype to another due to varying levels of variegation. The following detailed description of 'UF20-103-3' was obtained using ten-week-old plants grown from unrooted cuttings in February-April 2022 in a glass-covered greenhouse in Gainesville, Florida. The plants were propagated in mist for ten days after cuttings were stuck, then grown in one-gallon pots for approximately eight and a half additional weeks.

BOTANICAL DESCRIPTION

Botanical classification:
- *Family*.—Lamiaceae.
- *Botanical name*.—*Coleus scutellarioides*.
- *Common name*.—*Coleus*.
- *Cultivar*.—'UF20-103-3'.

Parentage:
- *Female or seed parent*.—'UF17-73-7'.
- *Male or pollen parent*.—Unknown.

Plant description:
- *Habit*.—Upright and spreading.
- *Height* (*from top of soil*).—40-45 cm.
- *Width* (*horizontal plant diameter*).—60-65 cm.

Propagation:
- *Type cuttings*.—Vegetative meristem tip cuttings having at least 1 node.
- *Time to initiate roots*.—3-4 days.
- *Time to produce a rooted cutting*.—7-10 days.
- *Root habit*.—Fibrous.
- *Root description*.—Callus forms in 2 to 3 days, roots initiate in 3-4 days and become a highly branched cutting in 7-10 days.

Branches:
- *Quantity per plant*.—Approximately 6.
- *Branch color*.—RHS 145C (light yellow green).
- *Texture*.—Smooth.
- *Pubescence*.—Not present.
- *Stem description*.—Square-shaped stem.
- *Branch diameter*.—0.7-0.8 cm at the base of a 35-cm-long branch.
- *Branch length*.—35-40 cm.
- *Internode length*.—5.5 cm measured at mid-branch.
- *Anthocyanin*.—Not present.

Foliage description:
- *Quantity of leaves per branch*.—18-20. Arrangement: Opposite.
- *Fragrance*.—Not fragrant.
- *Shape*.—Ovate.
- *Length*.—12-13 cm.
- *Width*.—11-12 cm.
- *Apex*.—Broadly acute.
- *Base*.—Attenuate.
- *Margin*.—Highly lobed.
- *Leaf texture*.—Upper surface: Pulverulent. Lower surface: Smooth.
- *Venation color*.—Upper surface, apex: RHS N186C (greyish red). Upper surface, base: RHS 161C (pale yellow). Lower surface: RHS 145A (yellow green).
- *Venation pattern*.—Upper surface: Reticulate. Lower surface: Reticulate.
- *Color, immature leaf*.—Upper surface, major color: RHS 187C (dark red). Upper surface, margins: RHS N144C (yellow green). Upper surface, base: RHS N144C (yellow green). Lower surface, major color: RHS 146C (yellow green). Lower surface, margins: RHS 144B (yellow green). Lower surface, area around veins: RHS N186A (purplish grey).
- *Color, mature leaf*.—Upper surface, major color: RHS 187A (dark red). Upper surface, margins: RHS N144C (yellow green). Upper surface, base: RHS 140A (yellowish green). Upper surface, spots: RHS 160B (light yellow). Lower surface, major color: RHS 139B (yellowish green). Lower surface, area around veins: RHS N186A (purplish grey).
- *Petiole length*.—Approximately 2.5 cm.
- *Petiole diameter*.—0.3-0.4 cm.
- *Petiole color*.—RHS 145A (yellow green).
- *Petiole texture*.—Smooth, no pubescence.

Flowers and seeds: Flowers and seeds have not been observed to date during formal trials in Gainesville, Florida.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Florida have been long-tailed or citrus mealybugs (*Pseudococcus* spp.), which occur on older stock plant material held in the greenhouse for over 3-4 months. Impatiens Necrotic Spot Virus (*Bunyaviridae*) has also been observed in plants confined in greenhouses with mixed crops (peppers) infected with Western flower thrips (*Frankliniella occidentalis*). The most common pathogen of this species in the U.S. is downy mildew (*Perononspora lamii*). This pathogen has been observed in stock materials grown closely together in cooler growing seasons.

COMPARISON WITH KNOWN CULTIVARS

When the new cultivar 'UF20-103-3' is compared to the commercial cultivar 'UF17-52-25' (U.S. Plant Pat. No. 34,041, commercial name "Copperhead"), 'UF20-103-3' has a yellow green coloration along the base of the upper surface of mature leaves that is broken into numerous spots, whereas 'UF17-52-25' has a yellow green coloration along the base of the upper surface of mature leaves that is more broadly open with little to no spotting.

What is claimed is:

1. A new and distinct *Coleus scutellarioides* plant named 'UF20-103-3' as shown and described herein.

* * * * *